US006567683B1

United States Patent
Knuettel

(10) Patent No.: US 6,567,683 B1
(45) Date of Patent: May 20, 2003

(54) APPARATUS AND METHOD FOR CONDUCTING NUCLEAR MAGNETIC RESONANCE EXPERIMENTS ON A MEMBER OF THE BODY OF A BIG ANIMAL

(75) Inventor: Bertold Knuettel, Rheinstetten (DE)

(73) Assignee: Bruker Medical GmbH, Ettlingen (DE)

( * ) Notice: Subject to any disclaimer, the term of this patent is extended or adjusted under 35 U.S.C. 154(b) by 264 days.

(21) Appl. No.: 09/648,213

(22) Filed: Aug. 25, 2000

(30) Foreign Application Priority Data

Aug. 27, 1999 (DE) .......................... 199 40 778

(51) Int. Cl.[7] ............................................... A61B 5/05
(52) U.S. Cl. ...................................... 600/410; 600/415
(58) Field of Search ............................... 600/410, 415, 600/421, 411; 324/318, 321, 307, 309

(56) References Cited

U.S. PATENT DOCUMENTS

| 4,981,136 | A | | 1/1991 | Chance | |
|---|---|---|---|---|---|
| 5,194,809 | A | * | 3/1993 | Lew | 324/309 |
| 5,519,372 | A | * | 5/1996 | Palkovich et al. | 335/216 |
| 5,541,515 | A | * | 7/1996 | Tsujita | 324/318 |
| 5,640,958 | A | * | 6/1997 | Bonutti | 600/415 |
| 5,772,595 | A | * | 6/1998 | Votruba et al. | 600/415 |
| 6,169,402 | B1 | * | 1/2001 | Oka et al. | 324/318 |

FOREIGN PATENT DOCUMENTS

| DE | 43 25 206 C2 | 4/1995 |
|---|---|---|
| DE | 198 40 405 A1 | 4/1999 |
| EP | 0 825 450 A2 | 2/1998 |
| EP | 0 913 122 A1 | 5/1999 |
| JP | 020036842 A | 2/1990 |

OTHER PUBLICATIONS

"hocks" of horses (http://www.bruker.de/medical/tmb/biospec/horse/index.htm *of Aug. 10, 1999, 16.48 hours*).

\* cited by examiner

*Primary Examiner*—Quang T. Van
(74) *Attorney, Agent, or Firm*—Weingarten, Schurgin, Gagnebin & Lebovici LLP

(57) ABSTRACT

An apparatus is disclosed for conducting nuclear magnetic resonance experiments on an extremity of a big animal, in particular a horse. The apparatus includes a magnet assembly for receiving the extremity. A housing is provided adapted to the shape of the big animal. The housing incorporates a protrusion for receiving the extremity. The protrusion is adapted to be inserted into the magnetic assembly. A radio frequency (rf) assembly is provided for irradiating rf signals on the extremity and/or for receiving nuclear magnetic resonance signals from the extremity. The rf assembly is adapted to be attached to the protrusion.

25 Claims, 3 Drawing Sheets

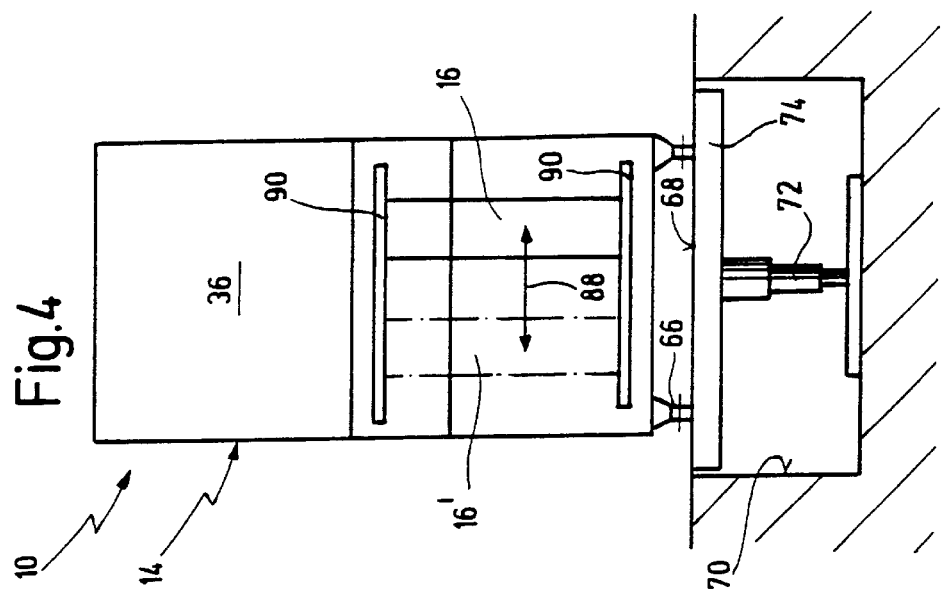
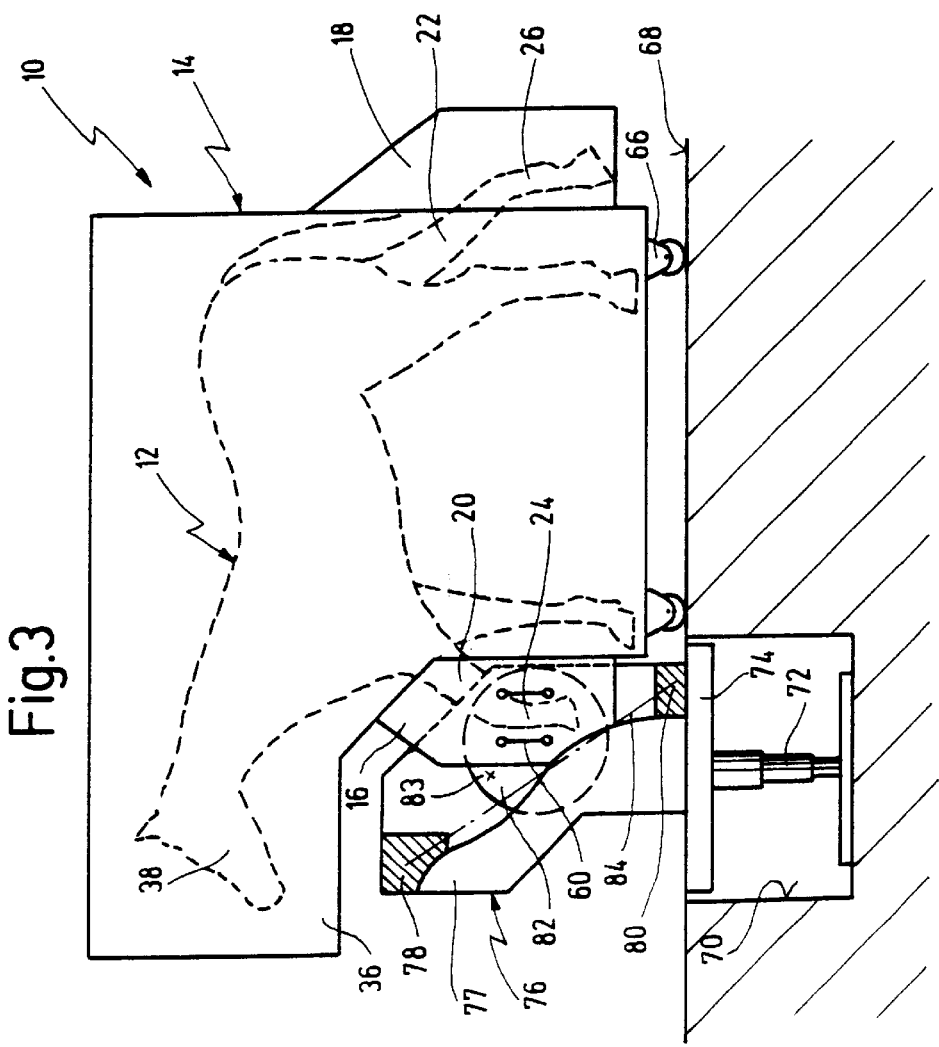

APPARATUS AND METHOD FOR CONDUCTING NUCLEAR MAGNETIC RESONANCE EXPERIMENTS ON A MEMBER OF THE BODY OF A BIG ANIMAL

FIELD OF THE INVENTION

The present invention is related to the field of magnetic resonance.

More specifically, the invention is related to medical applications of magnetic resonance, in particular with respect to veterinary applications on big animals.

Still more specifically, the invention is related to an apparatus for conducting nuclear magnetic resonance experiments on a member of the body, in particular an extremity of a big animal, comprising a magnet assembly for receiving the extremity and a radio frequency (rf) assembly for irradiating rf signals on the extremity and/or for receiving nuclear magnetic resonance signals from the extremity.

BACKGROUND OF THE INVENTION

It is well-known to utilize commercially available nuclear spin tomographs for examining the ankle joints, the so-called "hocks" of horses (http:\\www.bruker.de\medical\tmb\biospec\horse\index.htm of Aug. 10, 1999, 16.48 hours).

For such an examination the front leg or the rear leg of a horse must be brought into a solenoid coil of the nuclear spin tomograph, for conducting the measurements. As solenoid coils of commercially available nuclear spin tomographs have a horizontal axis, the horse for that purpose must be laid on its lateral side for introducing the front leg or the rear leg into the coil. As this is not the natural position for the horse, it is necessary to anesthetize the horse, at least to strongly sedate same. However, such manipulations on big animals, in particular on horses, are subject to substantial risks because horses react approximately five times as sensitively on anesthetics as compared to humans. Due to the inherent risks it is impossible to proceed as outlined above when extremely valuable big animals are to be examined, in particular racing horses.

U.S. Pat. No. 4,981,136 discloses a nuclear magnetic resonance apparatus for evaluating muscle efficiency and maximum power of muscle of a living animal, in particular a horse. This prior art apparatus utilizes a treadmill which is arranged such that a harnessed horse may run thereon. The treadmill extends through a very large solenoid coil. A measuring coil acting as a rf assembly for receiving signals for the nuclear resonance measurements is attached to the horse itself.

The prior art apparatus is, hence, extremely complicated and costly because a solenoid coil of about two meters inner diameter is required. Further, the mechanical components of the treadmill might cause substantial disturbances of the magnetic field. A precise examination of a specific member of the body of the horse, in particular of the horse's hock, is impossible for the simple reason that the ankles of the horse and, hence, the hocks are continuously moved when the horse is running.

EP 0 913 122 A1 discloses an examination table for imaging nuclear resonance measurements on extremities. The examination table has a design similar to that of a gynecologic examination chair. The patient lies on the examination table with one leg being spread away and resting in an elevated position on a cushion whereas the other leg, also spread away, is introduced into the measurement opening of a nuclear spin tomograph.

This examination table is, hence, only adapted to be used for the examination on humans.

EP 0 825 450 A2 discloses an apparatus for conducting nuclear resonance measurements on extremities of a human. The apparatus comprises a small solenoid coil being designed such that e.g. a hand may be introduced therein whereas the arm from the hand joint on is positioned outside the coil. For avoiding rf interferences, the arm is shielded with some kind of cuff.

This prior art apparatus is, hence, also solely intended to be used for humans who either hold still during the examination by their own will, i.e. because they feel responsible, or because they have been slightly sedated. An examination of big animals, in particular of horses, is impossible with this prior art apparatus.

It is, therefore, an object underlying the invention to improve an apparatus of the type specified at the outset, such that examinations on big animals, in particular on horses, become possible without the need of affecting the big animal more than absolutely necessary. By doing so it shall become possible to conduct measurements on highly valuable big animals, in particular on race horses which react highly sensitively on anesthetics or sedating agents.

SUMMARY OF THE INVENTION

According to the apparatus specified at the outset, this object is achieved in that the apparatus comprises a housing adapted to the shape of the big animal, that the housing comprises a protrusion for receiving the extremity, that the protrusion is adapted to be inserted into the magnet assembly, and that the rf assembly is adapted to be attached to the protrusion.

The object underlying the invention is thus entirely solved.

For, if a housing is used that is adapted to the shape of the big animal, the big animal may be brought into the housing and needs not to be sedated or anesthetized, in any event not to a larger extent. Big animals are frequently accustomed to such housings, for example horses being accustomed to corresponding transport vehicles within which horses may be transported within the normal traffic. A horse being accustomed to such a transport vehicle will certainly also enter into a housing adapted to its shape because it is accustomed to such a surrounding.

The use of a protrusion for receiving the body member has the advantage that the body member may be utilized for a measurement in an isolated position. A horse, for example, must only place one leg in front of the other so that the front leg may be subjected to an examination. It is then only necessary to introduce the protrusion into the magnet assembly and to operate a rf assembly attached to the protrusion correspondingly in order to conduct analytical or imaging nuclear resonance measurements as known per se.

In a preferred embodiment of the inventive apparatus, the housing encloses the big animal tightly.

This measure has the advantage that the animal is to a high degree fixed within the housing. The term "tightly", however, is to be understood to mean an arrangement allowing the big animal to essentially stand still in a predetermined position, thus avoiding that measuring artifacts are generated due to big movements. Such a "tight" housing is well-known to the big animal, as already mentioned, namely from corresponding transport vehicles which, too, are configured relatively tightly so that the animal is not injured during traveling, in particular during starting, during braking or when driving through a bend.

In another preferred embodiment of the inventive apparatus, the housing is configured impermeable for rf signals.

This measure has the advantage, known per se, that neither the high power rf exciting radiation may irradiate into the surrounding nor that radiation, for example radiation from radio or television stations may be irradiated into the housing and interfere with the measuring result. Only excitation signals will, therefore, be irradiated within the housing and will then be received and processed as corresponding measuring signals.

In a preferred embodiment of this variant, the housing, however, is provided with windows being permeable optically and/or permeable with respect to a room air condition.

This measure has the advantage that at least a visual contact with the big animal under examination is possible. This may, for example, be achieved in that a window is provided in the housing and the window is covered with a correspondingly tight screen acting as a Faraday cage for the rf signals of interest, whereas, on the other hand, it allows a visual contact with the big animal that may be calmed down by the physical presence of its owner. Moreover, an exchange of air and temperature thus becomes possible between the interior of the relatively tight housing and the surrounding atmosphere.

Moreover, it is preferred when the housing is provided with doors.

These doors may be configured relatively large for allowing an easy access to the housing. On the other hand the doors can also be configured relatively small for allowing a tactile contact with the big animal during the examination. In this connection a corresponding flexible shielding may be provided in the area of the doors, allowing to reach into the housing with the hand or with an arm without essentially altering or affecting the rf shielding when doing so.

Further, one may in a preferred manner provide the housing with a feeding device.

This measure has the advantage that the big animal may eat during the examination and is, hence, detracted therefrom.

For most applications it is preferred that the housing is adapted to receive the big animal in an upright position.

Moreover, it is preferred when the housing is mechanically reinforced in its bottom portion and in its wall portion adjoining the bottom portion.

This measure has the advantage that damaging of the housing may be prevented in case that the big animal, for example the horse, lashes out during the examination.

In other preferred embodiments of the invention, the housing is provided with fastening means for the body members or extremities.

This measure has the advantage that, if need arises, the body member under examination, for example, a front leg or a rear leg of a horse, may be fixed during the examination. By doing so, motion artifacts are minimized.

In still another group of embodiments of the invention, the protrusion is made detachable from the housing.

This measure has the advantage that the protrusion together with the rf assembly mounted thereto may be used for examining various body members, for example the right and the left front leg or the right and the left rear leg or for examining of all legs of a horse. An examination of the head and/or the neck of the horse is also possible in this way if a correspondingly dimensioned protrusion is used together with a magnet system having an air gap that may receive the protrusion.

For that purpose it is further preferred when the protrusion is adapted to be displaced on the housing.

This measure has the advantage that, for example, the right and the left front leg (or rear leg, respectively) of a horse may be examined one after the other without requiring substantial rearrangements on the apparatus and without the necessity to mount the relatively complicated rf assembly on four protrusions.

An especially good effect is, further, achieved when the magnet assembly comprises a magnet with an open air gap and the protrusion is adapted to be brought into the air gap.

This measure has the advantage that a relatively simple magnet assembly concept may be used and that the accessibility of the area of the homogeneous magnetic field may also be ensured quite simply.

In this regard it is, further, preferred when the magnet has an iron yoke.

This measure has the advantage that the magnet may be operated relatively simply. In an iron magnet having resistive exciting coils a mobile operation is theoretically possible, provided that a sufficiently strongly dimensioned source of electric current is available. It is, therefore, possible to operate the inventive apparatus, e.g. in stables, in race courses or at other places of action outside veterinary hospitals. As an alternative, permanent magnet poles could be utilized or superconducting coils.

In this regard it is, further, preferred when the magnet is a H-magnet or a U-magnet, preferably having an offset yoke plane.

This measure has the advantage that the air gap may be accessed very easily.

This holds true, in particular, when the magnet is positioned under an angle with respect to the vertical direction.

In that case it is, namely, possible to insert the protrusion along a horizontal direction, without running the risk of a collision with the yoke.

For that purpose it is, further, preferred when the magnet is adapted to be displaced in a horizontal and/or in a vertical direction and/or when the housing is adapted to be displaced in a horizontal and/or in a vertical direction.

These measures have the advantage that, as the case may be, an optimum sequence of movements between the magnet system and the housing is possible for bringing the protrusion into the magnet system.

As already mentioned, it is particularly preferred to utilize the inventive apparatus for measurements on horses, in particular for receiving a leg of a horse and, still more specifically, for conducting measurements on ankle joints or hocks of the horse.

The invention is, however, in now way limited to this application. Moreover, it can be used for numerous other measurements on big animals, and not only on extremities thereof but also on other body members, without leaving the scope of the present invention.

More advantages become apparent from the description and the enclosed drawing.

It goes without saying that the features mentioned before and those that will be explained hereinafter, may not only be used in the particularly given combination, but also in other combinations or alone without leaving the scope of the present invention.

BRIEF DESCRIPTION OF THE DRAWINGS

Embodiments of the invention are shown in the drawing and will be further discussed in the subsequent description.

Figure 1:
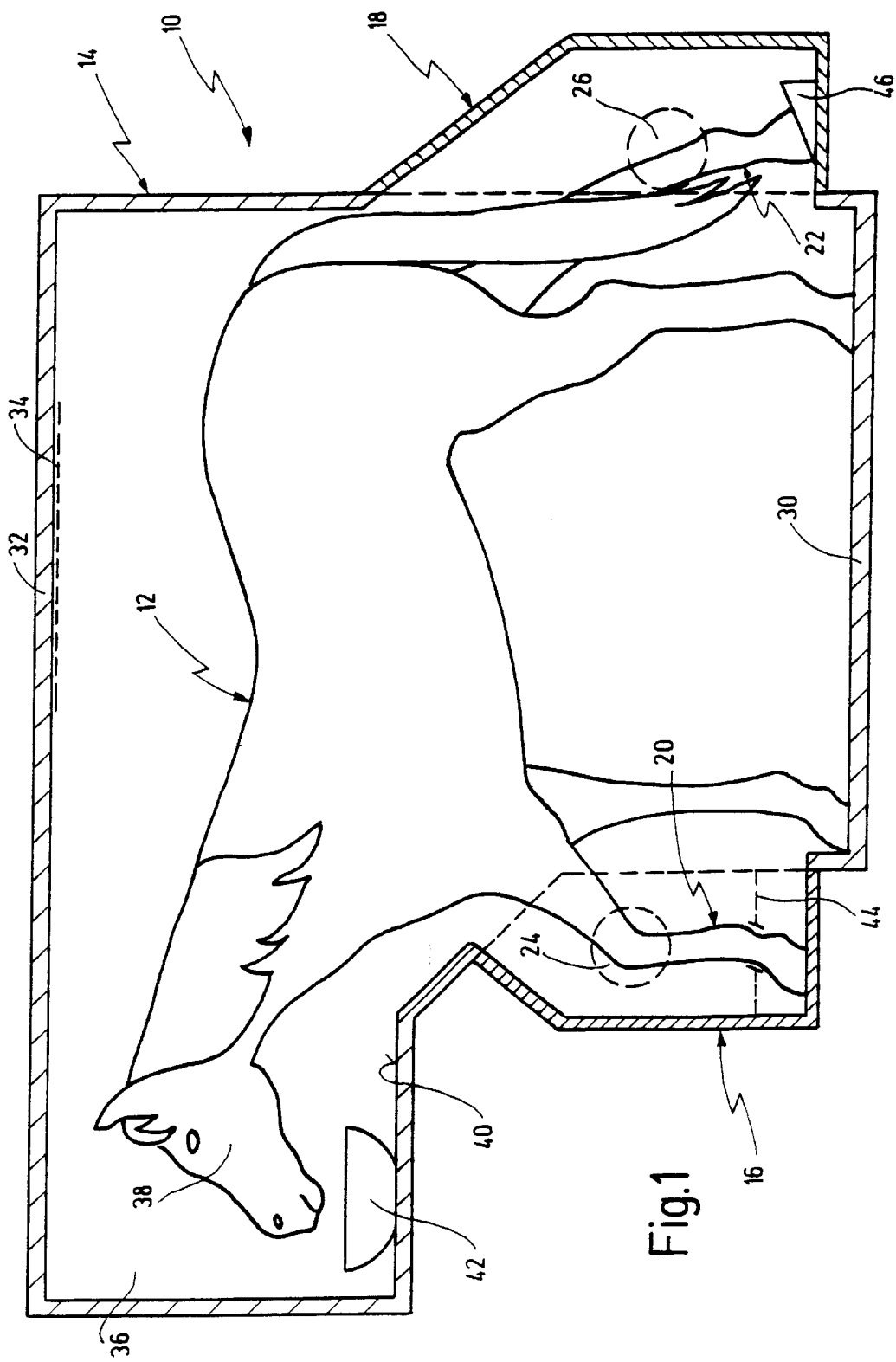
Figure 2:
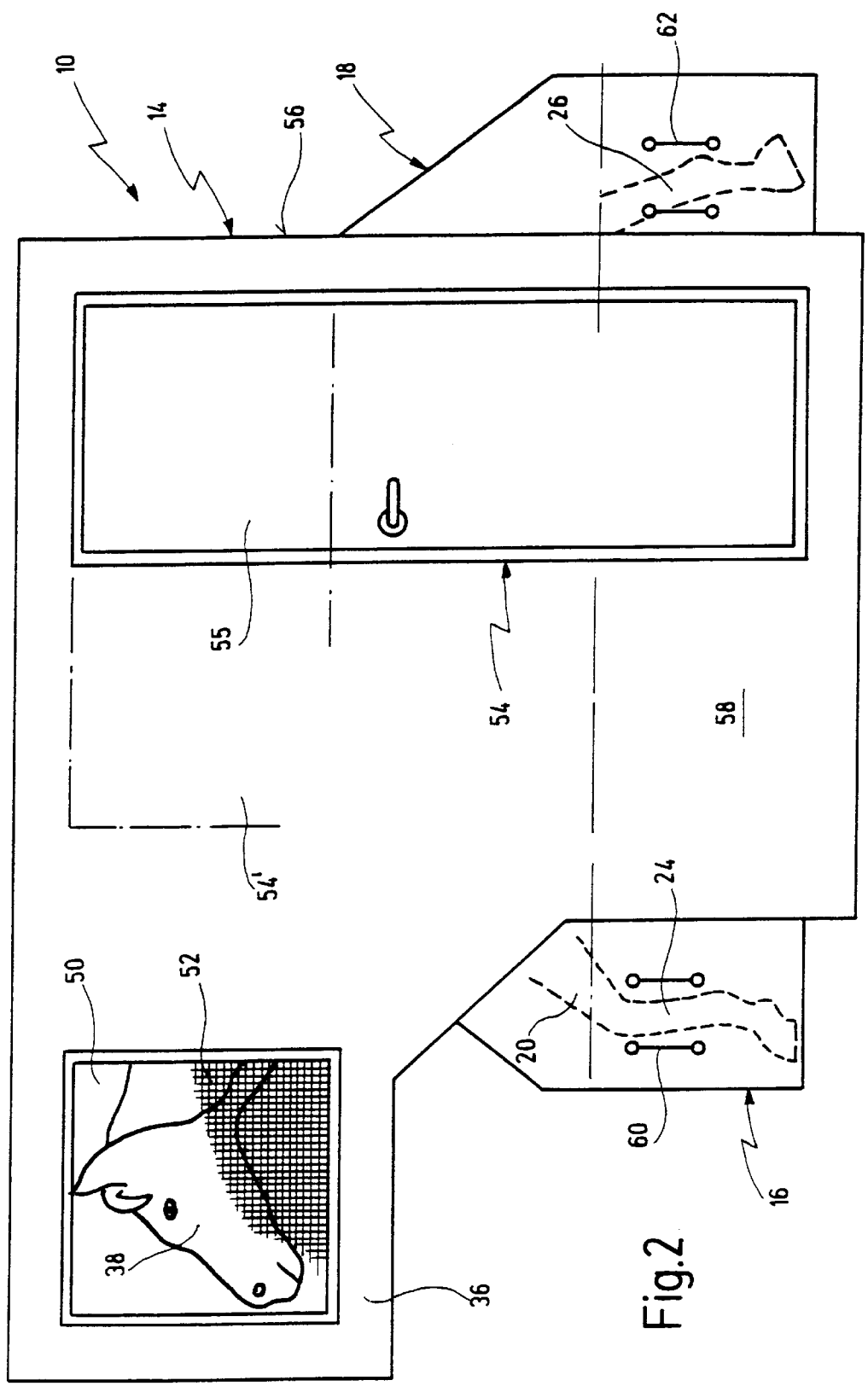

| | |
|---|---|
| FIG. 1 | shows a side elevational cross-sectional view of a housing as can be used on an embodiment of an inventive apparatus; |
| FIG. 2 | shows a side elevational view of the housing of FIG. 1 from outside; |
| FIGS. 3 and 4 | show further schematic side elevational and front elevational, respectively, views of the housing of FIGS. 1 and 2 together with a corresponding magnet system and corresponding adjustment units. |

DETAILED DESCRIPTION OF THE PREFERRED EMBODIMENTS

In the figures, reference numeral 10 as a whole designates a housing that is essentially adapted to the shape of a big animal 12, being a horse in the shown embodiment. Housing 10 consists of a main housing 14 for receiving the big animal 12 itself and of several protrusions, for example a first protrusion 16 at the front side and a second protrusion 18 at the rear side of housing 10. First protrusion 16 is adapted to receive a front leg 20 or, speaking in more general terms, a body member of the big animal 12, whereas second protrusion 18 is adapted to receive a back leg 22, or speaking in more general terms, also a body member of the big animal 12. Protrusions 16, 18 may also be provided at other positions for receiving other body members of the big animal, for example the head, the neck or other body members, the design being always adapted to the anatomy of the big animal to be examined.

In the embodiment shown, protrusions 16, 18 are adapted to physically isolate front leg 20 and rear leg 22, respectively, for enabling specific measurements, in particular on ankle joint or hock 24 and 26, respectively.

Such measurements are of particular importance for racing horses for allowing a judgment of the physical condition and the ability of the racing horse to perform, for taking the appropriate therapeutical measures, if necessary.

Housing 10 at its lower end is limited by a base plate 30 and at its upper end by a cover plate 32. On cover plate 32 reference numeral 34 indicates a radio frequency shielding covering the entire interior surface of housing 10 for making same "rf sealed". The term "rf sealed" is to be understood to mean a rf isolation of typically about 100 dB and more. The isolation prevents that the very strong rf measuring signals will be irradiated from the interior to the exterior of the housing and/or that the extremely sensitive receiver circuits within housing 10 are not affected by interference radiation from outside.

Housing 10 further, comprises a front portion 36 for receiving a head 38 of the big animal 12. Front portion 36 may be provided with a rest 40 for a feeding device 42. The big animal 12 may, hence, eat when being in housing 10 and is, therefore, distracted.

If necessary, the body member under examination, for example the front leg 20 or the back leg 22 may be fixed as indicated in FIG. 1 by a fastening device 44 for front leg 20.

On the other hand, depending on the individual anatomic circumstances, a support 46 may be provided allowing an inclined rest for a hoof or the like.

In FIG. 2, reference numeral 50 indicated a window being covered with a screen 52. Screen 52 acts as a Faraday cage and, hence, does not affect the rf isolation. On the other hand, screen 52 allows a visual contact between the owner or the caretaker of the big animal 12 and the big animal 12 so that it may be further calmed down by the presence of an accustomed person. Window 50, further, allows an exchange of air and temperature between the interior of housing 10 and the ambient atmosphere.

Reference numeral 54 indicates a door which, as shown, may either be located on a lateral wall or on a rear side 56 of housing 10. Door 54 allows access to housing 10, either for the owner or the caretaker of the big animal 12 or for the big animal 12 itself. Door 54 may be configured in various width, as indicated in FIG. 2 by dashed line 54'. An upper portion 55 of door 54 may, again, be provided with a screen, similar to screen 52. Door 54 may also be configured very small like a flap, allowing the caretaker of the big animal 12 to reach through this flap and to touch the big animal 12 for calming same. For that purpose a flexible rf lock may be provided, as described in EP 0 825 450 A2 mentioned at the outset.

In FIG. 2, reference numeral 58, further, indicated a bottom area that is configured with a mechanic reinforcement so that housing 10 is not damaged if the big animal 12 should lash out or kick due to nervousness.

Further, in FIG. 2, reference numeral 60 indicates a first rf assembly and 62 a second rf assembly on first protrusion 16 and on second protrusion 18, respectively. Rf assemblies 60, 62 are rf transmitter and receiver coils of conventional design. They are used to transmit exaltation signals for nuclear resonances and to receive nuclear resonance signals emitted by the tissue.

Rf assemblies 60, 62 are preferably positioned at the location of the measuring area on the object under examination. In the embodiment shown this is the area of the ankle joints 24 and 26.

The positioning, dimensioning and the detailed construction of rf assemblies 60, 62 is known to the person of ordinary skill and, hence, needs not to be explained in further detail in the present context.

FIGS. 3 and 4 show that housing 10 may be positioned on rollers 66 in order to allow housing 10 to be displaced along a horizontal plain. By doing so, housing 10 may be brought into a position in which it is located with the first protrusion 16 above a pit 20 or a corresponding step.

Pit 70 houses a hydraulic lift assembly 72 with a platform 74 supporting a magnet assembly 76.

Magnet assembly 76 comprises a H-magnet being shown in FIG. 3 in a partial sectional view and being deleted entirely in FIG. 4 for the sake of clarity. Magnet 77 comprises an upper yoke 78 and a lower yoke 80 defining an interconnecting plain 84 being tilted with respect to the vertical direction. Pole shoes 82 together with magnet coils (not shown) are positioned approximately at half distance between yokes 78 and 80. The yokes, however, may also configurate U-magnet. Resistive exiting coils are preferably used for magnet assembly 76, however, one could also use superconducting magnet coils or permanent magnet poles.

Pole shoes 82 enclose between them an air gap 83. Due to the tilted design of magnet 77, air gap 83 is accessible both from a lateral direction and from above. It is, therefore, possible to bring protrusion 16 into air gap 83 by displacing housing 10 from the right to the left and/or by displacing magnet 77 in a vertical direction by means of hydraulic lift assembly 72 so as to insert protrusion 16 into air gap 83. By doing so, the area of first rf assembly 60 may be positioned in the optimum area of air 83, i.e. within the magnetic field of highest homogeneity. The big animal 12 itself needs not to make any movements insofar.

Considering that protrusions 16 and 18 are quite complicated and expensive as structural units, in particular in view of the rf assemblies 60 and 62 mounted thereon and considering further that it is not necessary to examine more than one body member at one time, certain embodiments of the invention are configurated such that protrusions 16 and 18 are made detachable. By doing so, protrusions 16 and 18 may be attached to housing 10 at various positions for examining a corresponding body member of the big animal 12 at that position.

In the embodiment shown in the Figs., one type of protrusion 16 is provided for the front legs 22 and another type of protrusion is provided for the rear legs 22.

In order to enable to first examine the right front leg and thereafter the left front leg, protrusion 16 may be designed such that it can be shifted laterally on the front side of housing 10 as clearly shown in FIG. 4.

One may see rails 90 supporting protrusion 16 at its upper and its lower end and guiding same. Rails 90 extend horizontally, thus allowing to shift or displace protrusion 16 laterally (arrow 88) in order to bring it into the position for the left front leg and then to the position for the right front leg.

It goes without saying that this design is also made such that housing 10 remains rf sealed when protrusion 16 is displaced.

What is claimed is:

1. An apparatus adapted for conducting nuclear magnetic resonance experiments on an extremity of a non-reclining big animal having an external shape, the apparatus comprising:
    a magnet assembly for receiving said extremity,
    a housing adapted to surround said shape of said animal and incorporating a protrusion for separately enclosing said extremity, said protrusion being adapted to be inserted into an air gap of said magnet assembly, and
    a radio frequency (rf) assembly for irradiating rf signals on said extremity and/or for receiving nuclear magnetic resonance signals from said extremity, said rf assembly being adapted to be attached to said protrusion.
2. The apparatus of claim 1, wherein said housing encloses said big animal tightly.
3. The apparatus of claim 1, wherein said housing is configured impermeable for rf signals.
4. The apparatus of claim 3, wherein said housing is provided with optically transparent windows.
5. The apparatus of claim 3, wherein said housing is provided with windows being permeable with respect to a room air condition.
6. The apparatus of claim 1, wherein said housing is provided with doors.
7. The apparatus of claim 1, wherein said housing is provided with a feeding device.
8. The apparatus of claim 1, wherein said housing is adapted to receive said big animal in an upright position.
9. The apparatus of claim 8, wherein said housing is mechanically reinforced in a bottom portion thereof and in a wall portion adjoining said bottom portion.
10. The apparatus of claim 1, wherein said housing is provided with fastening means for attaching said extremity to said housing.
11. The apparatus of claim 1, wherein said protrusion is made detachable from said housing.
12. The apparatus of claim 11, wherein said protrusion is adapted to be displaced on said housing.
13. The apparatus of claim 1, wherein said magnet assembly comprises a magnet with an open air gap, said protrusion being adapted to be brought into said air gap.
14. The apparatus of claim 13, wherein said magnet has an iron yoke.
15. The apparatus of claim 14, wherein said magnet is a H-magnet.
16. The apparatus of claim 14, wherein said magnet is a U-magnet.
17. The apparatus of claim 14, wherein said magnet has an offset yoke plane.
18. The apparatus of claim 14, wherein said magnet is positioned under an angle with respect to a vertical direction.
19. The apparatus of claim 1, wherein said magnet is adapted to be displaced in a horizontal direction.
20. The apparatus of claim 1, wherein said magnet is adapted to be displaced in a vertical direction.
21. The apparatus of claim 1, wherein said housing is adapted to be displaced in a horizontal direction.
22. The apparatus of claim 1, wherein said housing is adapted to be displaced in a vertical direction.
23. The apparatus of claim 1, wherein said apparatus is adapted to be used for conducting measurements on a horse.
24. The apparatus of claim 23, wherein said protrusion is configured for receiving a leg of said horse.
25. The apparatus of claim 24, wherein said apparatus is configured for conducting measurements on a hock of said horse.

* * * * *